US008068647B2

(12) United States Patent
Lin

(10) Patent No.: US 8,068,647 B2
(45) Date of Patent: Nov. 29, 2011

(54) METHOD AND APPARATUS FOR REAL-TIME MOTION CORRECTION FOR ULTRASOUND SPATIAL COMPOUND IMAGING

(75) Inventor: Feng Lin, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 1532 days.

(21) Appl. No.: 11/152,653

(22) Filed: Jun. 14, 2005

(65) Prior Publication Data

US 2007/0014445 A1  Jan. 18, 2007

(51) Int. Cl.
*G06K 9/00* (2006.01)

(52) U.S. Cl. ...................................................... 382/128

(58) Field of Classification Search .................. 382/100, 382/128, 129, 130, 131, 132, 133, 134, 173, 382/181; 600/300, 407; 128/920; 378/1, 378/37, 21, 41, 42, 38, 44, 51, 62, 65, 146, 378/100, 128, 129, 130, 131, 132, 133, 134, 378/173, 181
See application file for complete search history.

(56) References Cited

U.S. PATENT DOCUMENTS

| | | | | |
|---|---|---|---|---|
| 4,649,927 | A * | 3/1987 | Fehr et al. | 600/443 |
| 5,555,534 | A * | 9/1996 | Maslak et al. | 367/135 |
| 6,126,599 | A * | 10/2000 | Jago et al. | 600/437 |
| 6,157,677 | A * | 12/2000 | Martens et al. | 375/240.16 |
| 6,283,917 | B1 | 9/2001 | Jago et al. | |
| 6,390,980 | B1 * | 5/2002 | Peterson et al. | 600/443 |
| 6,416,477 | B1 * | 7/2002 | Jago | 600/447 |
| 6,464,638 | B1 * | 10/2002 | Adams et al. | 600/443 |
| 2002/0120195 | A1 * | 8/2002 | Hossack et al. | 600/443 |
| 2003/0103567 | A1 * | 6/2003 | Riemens et al. | 375/240.16 |
| 2005/0041875 | A1 * | 2/2005 | Yamaguchi et al. | 382/233 |
| 2005/0288583 | A1 * | 12/2005 | Hirota | 600/437 |
| 2007/0092008 | A1 * | 4/2007 | Chang et al. | 375/240.16 |

FOREIGN PATENT DOCUMENTS

| | | |
|---|---|---|
| JP | 2005220138 | 8/1993 |
| JP | 2001521404 | 11/2001 |
| JP | 2002526225 | 8/2002 |
| JP | 2002526226 | 8/2002 |
| WO | 2004019058 | 3/2004 |

OTHER PUBLICATIONS

Xue et al., "A Motion Compensated Ultrasound Spatial Compounding Algorithm", Proceedings—19th International Conference. IEEE/EMBS Oct. 30-Nov. 2, 1997 Chicago, IL. USA, Digital Object Identifier: 10.1109/IEMBS.1997.757776, Available online: http://ieeexplore.ieee.org/stamp/stamp.jsp?tp=&arnumber=757776.*
Japanese Patent Office, Translation of Office Action pertaining to Japanese Patent Application No. 2004-000398, dispatched on Apr. 14, 2009 (3 pages).

* cited by examiner

*Primary Examiner* — Jingge Wu
*Assistant Examiner* — Tahmina Ansari
(74) *Attorney, Agent, or Firm* — Hanley, Flight & Zimmerman, LLC

(57) ABSTRACT

Certain embodiments of the present invention provide a method and system for real-time motion correction in compound ultrasound imaging. Certain embodiments include receiving an image frame, estimating motion between the image frame and a previous image frame, updating a previous motion estimate with the estimated motion to form an updated motion estimate, and correcting the image frame and the previous image frame using the updated motion estimate. The method may also include forming a compound image from the image frames. In an embodiment, motion may be estimated between the image frame and a previous frame using cross correlation, reference point registration, and/or other estimation method, for example. The image frame and the previous image frame may be corrected using the updated motion estimate in an affine transformation or other correction method, for example. In an embodiment, the method provides real-time correction as image frames are being received.

18 Claims, 5 Drawing Sheets

METHOD AND APPARATUS FOR REAL-TIME MOTION CORRECTION FOR ULTRASOUND SPATIAL COMPOUND IMAGING

RELATED APPLICATIONS

Not Applicable

FEDERALLY SPONSORED RESEARCH OR DEVELOPMENT

Not Applicable

MICROFICHE/COPYRIGHT REFERENCE

Not Applicable

BACKGROUND OF THE INVENTION

The present invention generally relates to ultrasound imaging. In particular, the present invention relates to real-time motion correction for ultrasound spatial compound imaging.

Ultrasound is sound having a frequency that is higher than a normal person may hear. Ultrasound imaging utilizes ultrasound waves or vibrations in the frequency spectrum above normal human hearing, such as the 2.5-10 MHz range. Ultrasound imaging systems transmit ultrasound into a subject, such as a patient, in short bursts. Echoes are reflected back to the system from the subject. Diagnostic images may be produced from the echoes. Ultrasound imaging techniques are similar to those used in sonar and radar.

A medical ultrasound system forms an image by sequentially acquiring echo signals from ultrasound beams transmitted to an object being imaged. An individual beam is formed by transmitting a focused pulse and receiving the echoes over a continuous range of depths. An amplitude of an echo signal decreases significantly for signal reflectors located deeper in the object due to increased signal attenuation of intervening structures, such as intervening tissue layers. Therefore, a signal-to-noise ratio decreases since noise generated by the ultrasound system's signal amplifiers, for example, may not be reduced to arbitrary low levels.

Forming the best possible image at all times for different anatomies and patient types is important to diagnostic imaging systems. Poor image quality may prevent reliable analysis of the image. For example, a decrease in image contrast quality may yield an unreliable image that is not usable clinically. Additionally, the advent of real-time imaging systems has increased the importance of generating clear, high quality images.

B-Mode or "Brightness" mode is a common display format for an ultrasound image. Currently, B-Mode ultrasound imaging system transducers fire a narrow ultrasound beam or vector in a single direction. The transducer array then waits to listen to all echoes returning from reflectors along that same straight line. Strength of the return echoes is used to represent a reflectivity of an object. Reflectivity of an object, such as an anatomy of a patient, is typically calculated using a range equation. The range equation determines that time equals signal round trip divided by speed of sound in a subject medium. Current ultrasound systems utilize receive beamforming to reconstruct an object being imaged. That is, an ultrasound system listens for echo signals using a receiver which is then used for beam reconstruction and beam directional determination. The scheme of firing an ultrasound beam and listening for reflected echoes is repeated sequentially in a number of directions to span a two-dimensional section in an object space, such as an anatomical space. The ultrasound system paints each line that is determined from the reflected echo signals with a brightness level corresponding to a return echo signal strength. A complete set of vectors that sweep out a section of space constitutes a B-Mode frame. The reconstruction process is repeated to successively paint frames and achieve a standard real-time B-Mode display.

Spatial compounding has become an advanced and important diagnostic tool in a wide range of applications in ultrasound imaging. In spatial compounding, a target is scanned from several angles of insonification or irradiation with sound or other such waves. Multiple received images are then combined or averaged to form a single image. A compounded image typically shows less speckle or interference introduced by scattering which degrades image resolution. A compounded image may also provide better specular reflector delineation than conventional ultrasound images from a single angle. In some ultrasound machines, multi-angle spatial compounding has been implemented on different types of transducers, such as a one-dimensional linear array and a one-dimensional curved linear array.

Spatial compound imaging improves contrast resolution by reducing speckles and enhancing tissue boundaries. However, a spatial compounded image is a summation of a series of frames, which are collected at different times. Consequently, spatial compounding is susceptible to motion, such as tissue or probe motion. Additionally, imaging with an extended field of view results in blurriness or artifacts from regular motion. Therefore, an improved method and apparatus for reducing or eliminating motion effects, such as blurriness, in a spatial compounded image would be highly desirable.

BRIEF SUMMARY OF THE INVENTION

Certain embodiments of the present invention provide a method and system for real-time motion correction in compound ultrasound imaging. Certain embodiments provide a method including receiving an image frame, estimating motion between the image frame and a previous image frame, updating a previous motion estimate with the estimated motion to form an updated motion estimate, and correcting one or more previous image frame(s) using the updated motion estimate. The method may also include forming a compound image from the image frames.

In an embodiment, motion may be estimated between the image frame and a previous frame using cross correlation, reference point registration, and/or other estimation method, for example. The image frame and the previous image frame may be corrected using the updated motion estimate in an affine transformation or other correction method, for example. In an embodiment, the method provides real-time correction as image frames are being received.

Certain embodiments provide a method for improved compound ultrasound imaging. The method include receiving an image frame, estimating motion between the image frame and a previous image frame, correcting the image frame and the previous image frame using the motion estimate, and forming a compound image from the image frames. The method may also include updating a previous motion estimate with the motion estimate to form an updated motion estimate. In an embodiment, motion between the image frame and a previous image frame may be estimated using at least one of cross correlation and reference point registration, for example. In an embodiment, the image frame and the previous image frame may be corrected using the motion estimate in an affine transformation, for example.

Certain embodiments provide a computer-readable medium including a set of instructions for execution on a computer. The set of instructions include a motion estimation routine configured to estimate motion between a new frame and a previous frame in a compound image set, a motion correction routine configured to correct frames in the compound image set based on the estimated motion, and an image compounding routine configured to combine frames in the compound image set to form a compound image. The set of instructions may also include a display routine for displaying a spatial compound image, for example.

In an embodiment, the motion correction routine aligns old frames to the new frame based on the estimated motion. In an embodiment, the motion estimation routine updates a previous estimated motion with the estimated motion to form an updated estimated motion. In an embodiment, the motion estimation routine selects the previous frame from at least one of a temporally adjacent frame, a spatially adjacent frame, a last same-angle frame, and a last compounded image, for example.

Certain embodiments provide a system for spatial compound ultrasound imaging. The system includes a frame buffer capable of storing a plurality of frames to form a compound ultrasound image, a memory capable of storing data including a motion estimate, and a processor configured to estimate motion between a new frame and a previous frame from the frame buffer. The processor is capable of correcting frames in the frame buffer based on the estimated motion. The processor combines frames in the frame buffer to form a spatial compound image.

In an embodiment, the new frame replaces an oldest frame in the frame buffer, for example. The processor may sum frames in the frame buffer to form the spatial compound image. The processor may select the previous frame from at least one of a temporally adjacent frame, a spatially adjacent frame, a last same-angle frame, and a last compounded image, for example. In an embodiment, the processor models the estimated motion as at least one of rigid, affine and elastic, for example. The processor may also apply spatially variant shading to frame data in the frame buffer.

Figure 1:
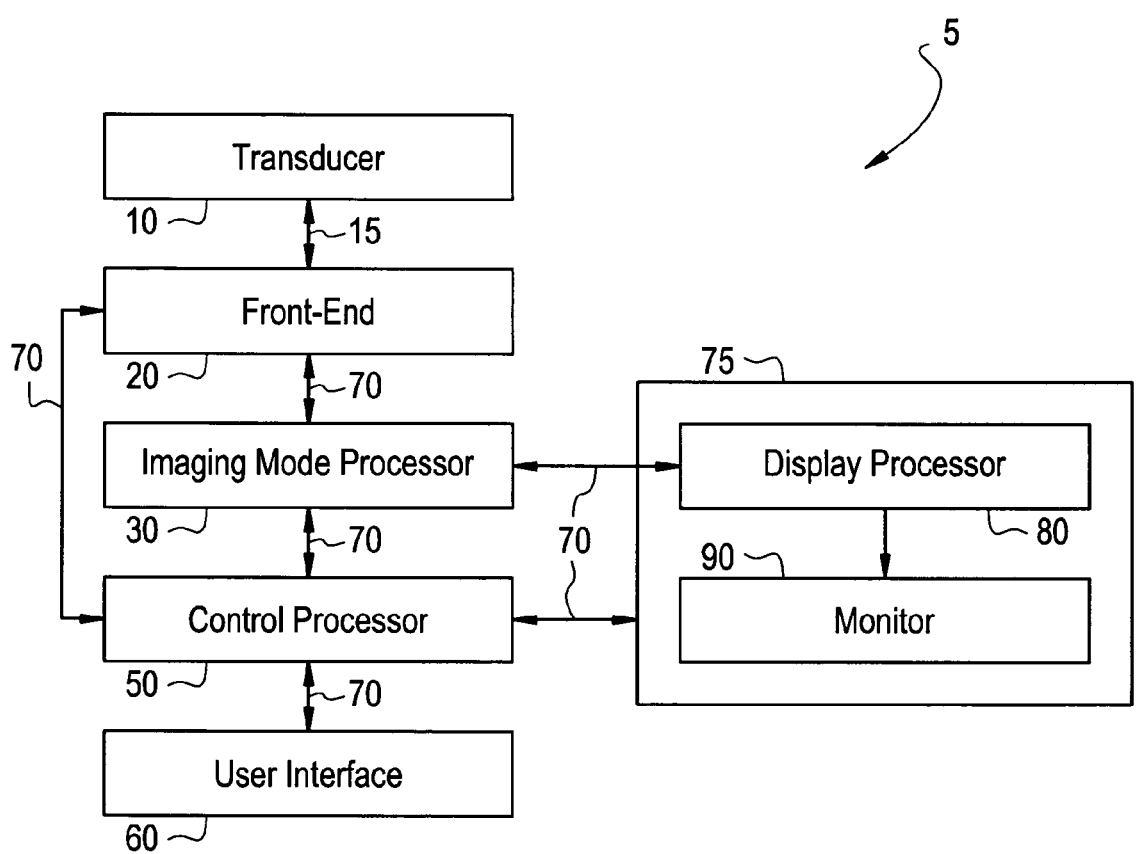
FIG. 1 illustrates a block diagram of an ultrasound imaging system used in accordance with an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

FIG. 1 illustrates a block diagram of an ultrasound imaging system 5 used in accordance with an embodiment of the present invention. The system 5 includes a transducer 10, a front-end 20, an imaging mode processor 30, a user interface 60, a control processor 50, and a display 75. The imaging mode processor 30 and the control processor 50 may be part of a back-end system, for example. The transducer 10 is used to transmit ultrasound waves into a subject by converting electrical analog signals to ultrasonic energy. The transducer 10 may also be used to receive ultrasound waves that are backscattered from the subject by converting ultrasonic energy to analog electrical signals. The front-end subsystem 20, including a receiver, a transmitter, and a beamformer, is used to create transmitted waveforms, beam patterns, receiver filtering techniques, and demodulation schemes that are used for various imaging modes. The front-end 20 converts digital data to analog data and vice versa. The front-end 20 interfaces with the transducer 10 via an analog interface 15. The front-end 20 interfaces with the imaging mode processor 30 and the control processor 50 via a digital bus 70. The digital bus 70 may include several digital sub-buses. The digital sub-bases may have separate configurations and provide digital data interfaces to various parts of the ultrasound imaging system 5.

The imaging mode processor 30 provides amplitude detection and data compression for an imaging mode, such as B-mode imaging, M-mode imaging, BM-mode imaging, harmonic imaging, Doppler imaging, color flow imaging, and/or any other ultrasound imaging mode. The imaging mode processor 30 receives digital signal data from the front-end 20. The imaging mode processor 30 processes the received digital signal data to produce estimated parameter values. The estimated parameter values may be produced using the received digital signal data. The digital signal data may be analyzed in frequency bands centered at the fundamental, harmonics, or sub-harmonics of the transmitted signals to produce the estimated parameter values. The imaging mode processor 30 passes the estimated parameter values to a control processor 50 over the digital bus 70. The imaging mode processor 30 may also pass the estimated parameter values to the display 75 via the digital bus 70.

The display 75 includes a display processor 80 and a monitor 90. The display processor 80 accepts digital parameter values from the imaging mode processor 30 and the control processor 50. The display processor 80 may perform scan-conversion functions, color mapping functions, and tissue/flow arbitration functions, for example. The display processor 80 processes, maps, and formats the digital data for display, converts the digital display data to analog display signals, and passes the analog display signals to the monitor 90. The monitor 90 accepts the analog display signals from the display processor 80 and displays the resultant image. An operator may view the image on the monitor 90.

The user interface 60 allows user commands to be input by the operator to the ultrasound imaging system 5 through the control processor 50. The user interface 60 may include a keyboard, mouse, switches, knobs, buttons, track ball, and/or on screen menus, for example.

The control processor 50 is the central processor of the ultrasound imaging system 5. The control processor 50 interfaces to other components of the ultrasound imaging system 5 using the digital bus 70. The control processor 50 executes various data algorithms and functions for various imaging and diagnostic modes. Digital data and commands may be transmitted and received between the control processor 50 and other components of the ultrasound imaging system 5. In an alternative embodiment, functions performed by the control processor 50 may be performed by multiple processors and/or may be integrated into the imaging mode processor 30 and/or the display processor 80. In another embodiment, the functions of the processors 30, 50, and 80 may be integrated into a single personal computer (PC) backend.

Figure 2:
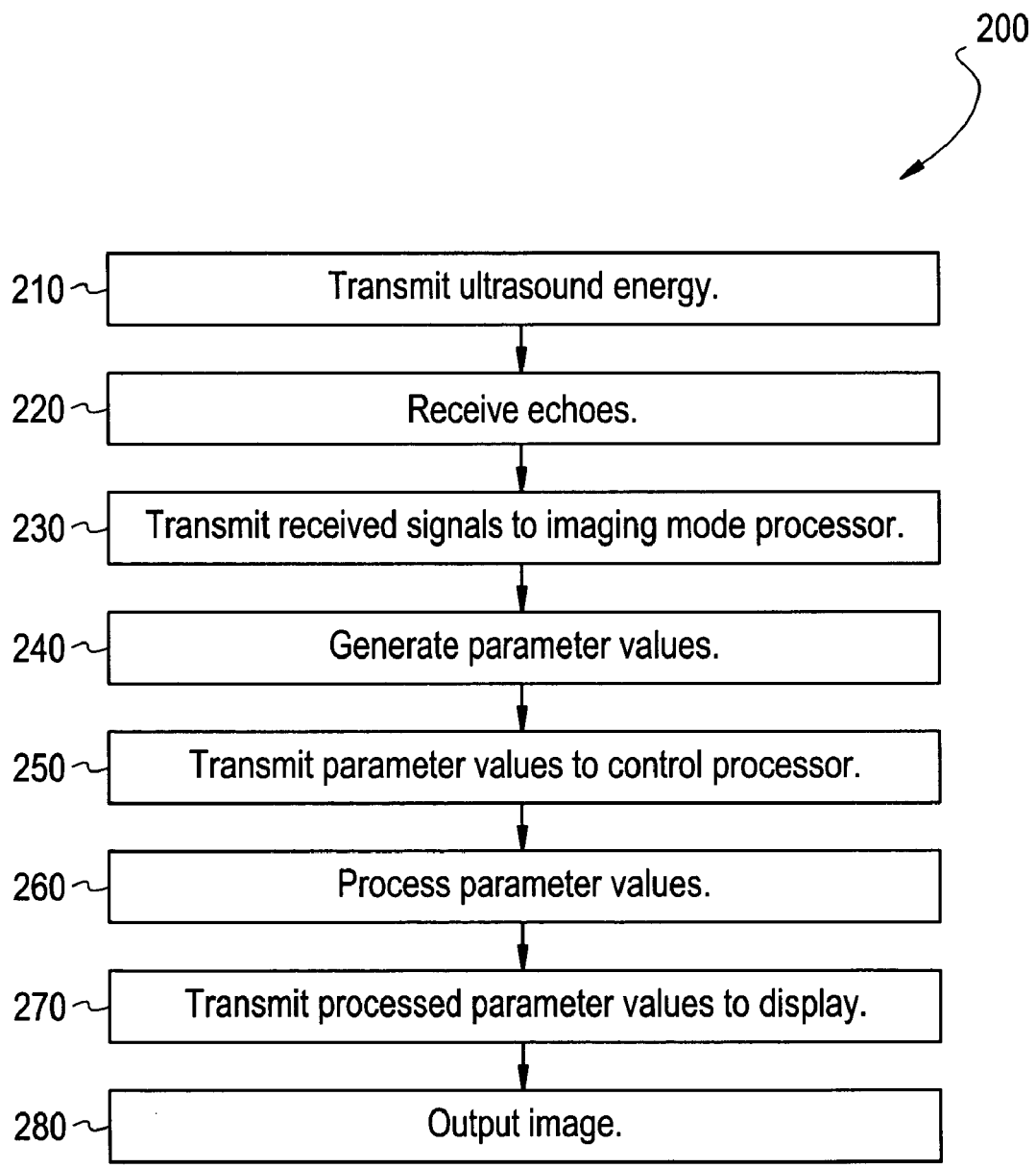
FIG. 2 illustrates a flow diagram for a method for ultrasound imaging in accordance with an embodiment of the present invention.

FIG. 2 illustrates a flow diagram for a method 200 for ultrasound imaging in accordance with an embodiment of the present invention. First, at step 210, the transducer 10 transmits ultrasound energy into a subject, such as a patient. Then, at step 220, ultrasound energy or echoes backscattered from the subject are received at the transducer 10. Signals are received at the front-end 20 in response to ultrasound waves backscattered from the subject.

Next, at step 230, the received signals are transmitted from the front-end 20 to the imaging mode processor 30 using the digital bus 70. At step 240, the imaging mode processor 30 generates parameter values based on the received signals. Then, at step 250, the parameter values are sent to the control processor 50.

At step 260, the control processor 50 processes the parameter values for use in display, storage, and diagnostics at the display 75. The control processor 50 processes the image data parameter values to reduce artifacts and process resulting image(s). The control processor 50 and/or imaging mode processor 30 may compound image data to produce a compound image. For example, image data from a plurality of angles may be combined or averaged to produce a spatially compound image.

Next, at step 270, processed parameter values are transmitted to the display 75. The display processor 80 may also process parameter values from a plurality of focal zone images to produce a combined image in conjunction with and/or in addition to the control processor 50.

Finally, at step 280, a diagnostic image is produced and output at the monitor 90. The image may be stored, displayed, printed, and/or further transmitted, for example. The display processor 80 may produce the diagnostic image using the processed parameter values from the digital signal data.

For implementation of spatial compound imaging, some ultrasound imaging systems use full fundamental or full harmonic transmission in all directions. Received echo signal data is then combined to form an image. Using a single transmit fundamental frequency may result in severe grating lobe artifacts. Decreasing transmit signal frequency as transmission angle decreases may help reduce the grating lobes. However, decreasing transmitting signal frequency results in degradation of signal resolution. On the other hand, harmonic transmissions have fewer grating lobes than fundamental frequencies. However, harmonic transmission provides less penetration than fundamental frequency transmission.

In an embodiment, fundamental and harmonic frequency transmissions are combined to produce a resulting image. For small steering angles with little or no grating lobes, fundamental frequencies may be transmitted. For large steering angles, more grating lobes are produced, so harmonic frequencies may be transmitted. Fundamental and harmonic echo signals may be processed and combined to produce one or more images. By combining fundamental and harmonic signals where appropriate based on beam steering angle, speckle may also be smoothed more effectively. Low or high frequency fundamental transmissions, as well as single, double or coded harmonics as disclosed in U.S. patent application "Method and Apparatus for Tissue Harmonic Imaging with Natural (Tissue) Decoded Coded Excitation", application Ser. No. 10/679,542, filed on Oct. 6, 2003, by Xiaohui Hao et. al., for example, which is herein incorporated by reference, may also be used and combined with other fundamental and/or harmonic signals. The imaging mode processor 30 or other hardware or software determines which kind of signals to fire from the transducer 10 into an object to be imaged.

Certain embodiments provide a compound imaging technique that maintains spatial resolution while reducing grating lobes. Frequencies are lowered for angle steering, and harmonic imaging is used when the steering angle is greater than 0, for example. In an embodiment, frequency compounding (or variable frequency imaging) may be employed, as disclosed in a patent application entitled "Method and Apparatus for Ultrasonic Speckle Reduction Using Wideband Frequency Compounding with Tissue-Generated Harmonics", application Ser. No. 10/335,277, filed on Dec. 31, 2002, by Feng Lin et. al., which is herein incorporated by reference. Additionally, ultrasound compound imaging with combined fundamental and harmonic signals, as disclosed in patent application "Method and Apparatus for Ultrasound Compound Imaging with Combined Fundamental and Harmonic Signals", application Ser. No. 10/703,903, filed on Nov. 7, 2003, by Xiaohui Hao et al., which is herein incorporated by reference, may be used to help improve speckle suppression.

Figure 3:
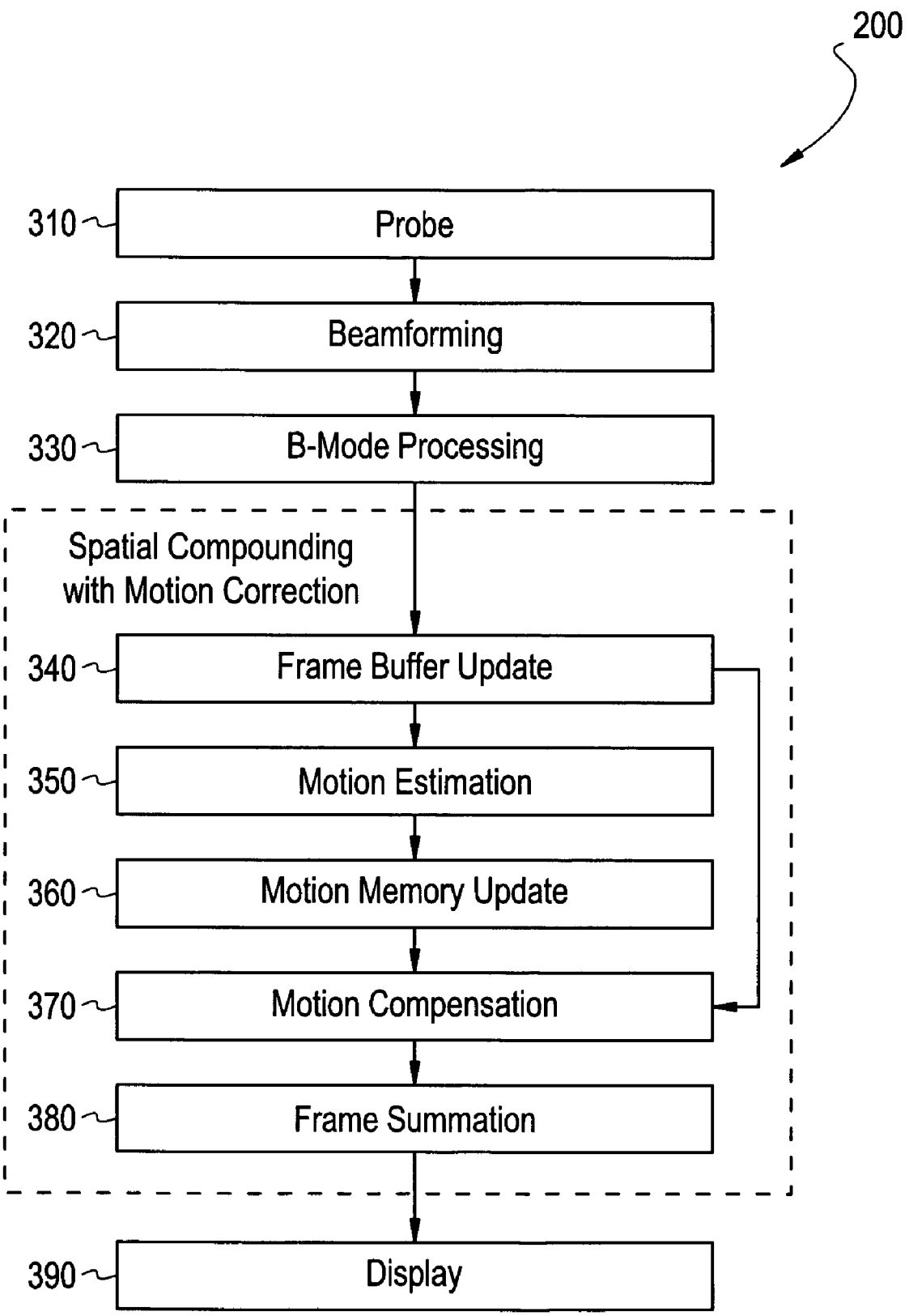
FIG. 3 illustrates an improved spatial compounding system used in accordance with an embodiment of the present invention.

FIG. 3 illustrates an improved spatial compounding system 300 used in accordance with an embodiment of the present invention. The system 300 may be used to estimate and compensate for motion between frames for spatial compounding. The system 300 includes a probe 310, a beamforming module 320, a B-mode processing module 330, a frame buffer update module 340, a motion estimation module 350, a memory update module 360, a motion compensation module 370, a frame summation module 380, and a display 390. Components of the system 300 may be implemented in software and/or in hardware. Components of the system 300 may be implemented separately and/or may be combined in various forms, for example. While the system 300 may operate using any ultrasound imaging mode, the description below is illustrated using b-mode ultrasound imaging for exemplary purposes only.

In operation, echoes received from the probe 310 are first focused in the beamforming block 320. B-mode frames are then formed in the b-mode processing block 330 and stored in the frame buffer 340. A number of total frames in the frame buffer 340 may be N+1, where N is a number of frames used to construct a compounded image. Each time a new frame is formed, the oldest frame in the frame buffer 340 is removed and replaced by the new frame. In the motion estimation block 350, motion between the new frame and a previous frame is estimated. The estimated motion is then used to update the existing motion information stored in the motion memory 360. The motion information describes the motion between all the frames to be used to construct a compounded image. In the motion compensation block 370, the old frames are aligned to the new frame based on the updated motion information. The aligned frames are summed in the compounding block 380. The compounded image is finally displayed at the display 390.

Certain embodiments operate in an "update" mode. Since motion between old frames have been estimated before the new frame is received, each time a new frame arrives, only one motion is estimated between the new frame and a previous frame. The previous frame may be chosen to be a temporally adjacent frame, a spatially adjacent frame, a last same-angle frame, or a last compounded image, for example. If a temporally adjacent frame is chosen, for example, tissue has least motion and distortion but images may not resemble each other because the images may be scanned from different angles. If a same-angle frame is chosen, scanned images resemble each other since steering angles are the same but the images may be temporally far away. Characteristics of spatially adjacent frame and a last compounded image may lie in between the same-angle frame and the temporally adjacent frame, for example.

Figure 4:
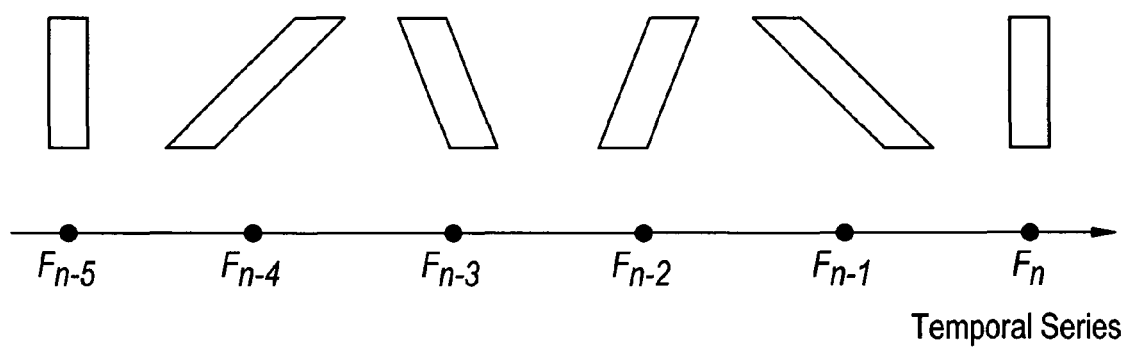
FIG. 4 shows a temporal sequence of frames used in accordance with an embodiment of the present invention.

FIG. 4 shows a temporal sequence of five compound frames used in accordance with an embodiment of the present invention. For new frame $F_n$, frame $F_{n-1}$ is a temporal neighbor, frames $F_{n-2}$ and $F_{n-3}$ are spatial neighbors, frame $F_{n-5}$ is a same-angle frame, and the last compounded image is a summation from $F_{n-5}$ to $F_{n-1}$ after registration. The motion may be estimated by any existing methods, e.g., a cross correlation method. The motion may be modeled to be rigid, affine, or elastic, depending on a desired trade-off between accuracy and complexity, for example.

In an embodiment, without losing generality, motion from frame j to frame i may be represented as $U_{ij}$, motion from frame i to frame j may be represented as $U_{ji}=U_{ij}^{-1}$, and alignment may be represented by $f_j'=U_{ij}f_j$, where $f_j$ is the original frame and $f_j'$ is the frame j aligned to frame i. The motion $U_{ik}$ may be derived from $U_{ij}$ and $U_{jk}$ using $U_{ik}=U_{ij}U_{jk}$. In an embodiment, motion between the same frame $U_{ii}$ is a unit and is noted as 1.

In the motion memory 360, the motion between each previous frame and the current frame $\{U_{ni}, i=n, n-1, n-2, \ldots\}$ is stored, where n is the current frame. When a new frame n+1 is formed, the motion $U_{(n+1)j}$ is first estimated, where j is a chosen previous frame. The new motion set may then be computed by $$U_{(n+1)i} = \begin{cases} U_{(n+1)j}U_{nj}^{-1}U_{ni} & i=n, n-1, \cdots \\ 1 & i=n+1. \end{cases} \quad \text{(Equation 1)}$$

Spatially variant shading may be applied to frame data, for example. The shading may have multiple benefits such as reducing edge artifacts and improving image uniformity. An example of shading for spatial compound imaging using weighted image data is described in a patent application entitled "Range Dependent Weighting for Spatial Compound Imaging", application Ser. No. 10/914,326, filed on Aug. 9, 2004, by Michael Washburn et. al., which is herein incorporated by reference. To avoid undesired artifacts, shading may be first applied on the frame data, and then motion correction may be made on both the shaded data and the shading itself. The aligned frame data and shading are summed, and the compounded data are calculated by normalizing the frame sum using the shading sum:

$$f_c = \frac{\sum_i U_{(n+1)i}(w_i f_i)}{\sum_i U_{(n+1)i} w_i}. \quad \text{(Equation 2)}$$

Figure 5:
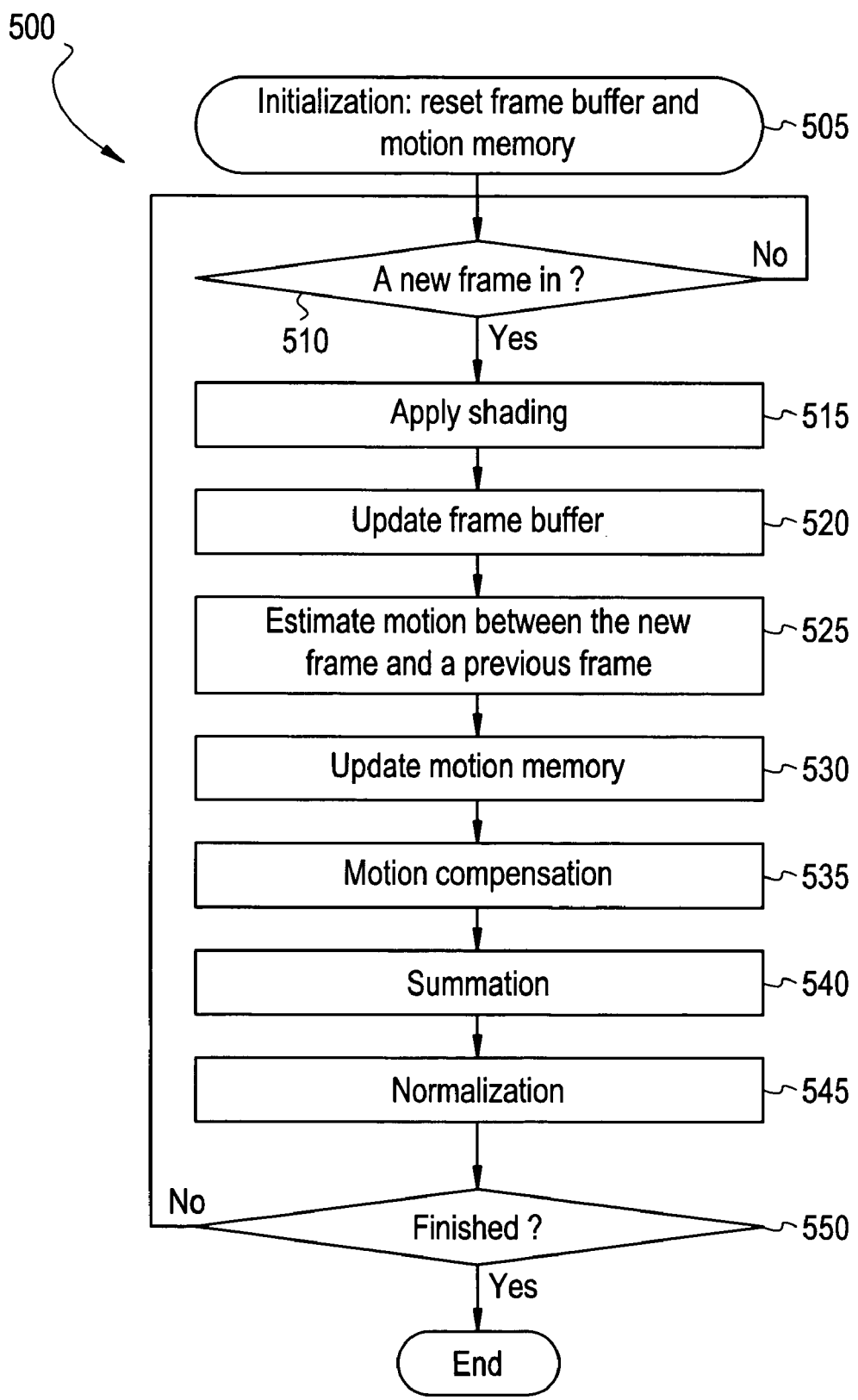
FIG. 5 illustrates a flow diagram for a method for improved compound imaging with motion correction used in accordance with an embodiment of the present invention.

FIG. 5 illustrates a flow diagram for a method 500 for improved compound imaging with motion correction used in accordance with an embodiment of the present invention. First, at step 505, motion correction is initialized. For example, the frame buffer and motion memory are reset. Then, at step 510, receipt of a new frame is determined. If a new frame has not been received, the motion correction method may end or may wait for a new frame to be received, for example. If a new frame has been received, then, at step 515, shading is applied to the new frame data. Shading, such as spatially variant shading, may be used to reduce edge artifacts and smooth an image to promote uniformity. At step 520, the frame buffer is updated with the shaded data.

Next, at step 525, motion is estimated between the new frame and a previous frame. For example, since frames may be acquired at different times, movement in tissue and/or probe may introduce motion artifacts or differences in objects between frames. A comparison of the new frame and a previous frame, such as a comparison of image data, may reveal an estimated motion effect between the frames. In certain embodiments, one or more methods, such as cross correlation and/or registration based on reference points, may be used to estimate motion between frames. At step 530, motion memory is updated with the motion estimate. For example, motion information stored in the motion memory is updated or otherwise modified with the motion estimate.

Then, at step 535, motion compensation is performed on the image frames. For example, the motion information is used to compensate for motion effects in the frames. The old frames may be aligned to the new frame using motion information, for example. Various methods of motion correction may be used to compensate for motion effects between frames.

For example, affine transformation may be used to compensation for motion effects in frames. An affine transformation is any transformation that preserves collinearity and distance ratios in an image. That is, all points initially located along a line are still located along that line after transformation, and a midpoint of a line segment remains the midpoint of the line segment after transformation. Examples of affine transformations include geometric contraction, expansion, dilation, reflection, rotation, shear, similarity transformations, spiral similarities, translation, combinations of the above and/or other composition of rotations, translations, dilations, and shears. For example, if the motion between frames is modeled by an affine transformation, then a scale factor s, a rotation angle alpha, an initial x-coordinate position x0, and an initial y-coordinate position y0 are first evaluated in motion estimation. In motion compensation, affine transformation is made using the calculated s, alpha, x0, and y0, as shown in the following equations:

$$x'=(s \cos \alpha)x+(s \sin \alpha)y-s(x_0 \cos \alpha+y_0 \sin \alpha)$$

$$y'=(-s \sin \alpha)x+(s \cos \alpha)y+s(x_0 \sin \alpha-y_0 \cos \alpha).$$

At step 540, frames are summed to form a compound image. For example, the aligned frames may be spatially summed to form a spatial compound image. Then, at step 545, after the compound image has been formed, the compound image data is normalized. Next, at step 550, if additional new image frames are to be processed, the method repeats at step 510. Shading, motion information, motion compensation, etc. are adjusted based on the new frame. If no new image frames are to be processed, motion correction for the compound image ends. The corrected compound image may be stored, displayed, and/or transmitted, for example.

Thus, certain embodiments provide an efficient method and system for real-time motion correction for ultrasound spatial compound images. Certain embodiments provide motion correction as frames are being received and/or after frames have been received and may accommodate any number of frames for processing. Certain embodiments produce a compound image that has been properly aligned prior to compounding.

Certain embodiments obtain one motion estimate per frame update because a previous estimation is stored. Using the offset between previous frames, one estimate comparing the new frame to a previous frame enables identification of relationships between the frames and alignment adjustment for a compound image with reduced motion effects.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A method for real-time motion correction in compound ultrasound imaging, said method comprising:
   receiving a new image frame;
   updating a frame buffer with said new image frame, said new image frame replacing an oldest image frame in said frame buffer;
   applying spatially variant shading to frames in said frame buffer;
   estimating motion between said new image frame and a previous image frame in said frame buffer to form an estimated motion, said new and previous image frames including spatially variant shading;
   updating stored motion information with said estimated motion, said stored motion information describing motion between all frames to be used to construct a compounded image;
   aligning image frames in said frame buffer to said new image frame based on said updated motion information; and
   forming a compound image from said image frames in said frame buffer.

2. The method of claim 1, wherein said estimating further comprises estimating said motion between said new image frame and a previous image frame using at least one of cross correlation and reference point registration.

3. The method of claim 1, wherein said correcting further comprises correcting said new image frame and said previous image frame using said updated motion estimate in an affine transformation.

4. A method for improved compound ultrasound imaging, said method comprising:
   receiving a new image frame;
   updating a frame buffer with said new image frame, said new image frame replacing an image frame in said frame buffer;
   applying spatially variant shading to frames in said frame buffer;
   estimating motion between said new image frame and a previous image frame in said frame buffer to form an updated motion estimate, said new and previous image frames including spatially variant shading, wherein said estimated motion represents one motion estimate between said new image frame and said previous image frame;
   updating stored motion information with said estimated motion, said stored motion information describing motion between frames to be used to construct a compounded image;
   aligning said previous image frame to said new image frame using said updated motion information; and
   forming a compound image from said image frames in said frame buffer.

5. The method of claim 4 wherein said estimating further comprises estimating said motion between said new image frame and a previous image frame using at least one of cross correlation and reference point registration.

6. The method of claim 4, wherein said correcting further comprises correcting said new image frame and said previous image frame using said motion estimate in an affine transformation.

7. A non-transitory computer-readable medium storing a set of instructions for execution on a computer, said set of instructions comprising:
   a motion estimation routine configured to estimate motion between a new frame and a previous frame in a compound image set, said motion estimate routine to estimate motion between said new frame and said previous frame from a frame buffer to which spatially variant shading has been applied, wherein said motion estimation routine dynamically updates stored motion information with said estimated motion, said stored motion information describing motion between all frames to be used to construct a compounded image;
   a motion correction routine configured to correct frames in said compound image set based on said estimated motion, wherein said motion correction routine aligns old frames to the new frame based on said updated motion information; and
   an image compounding routine configured to combine frames in said compound image set to form a compound image.

8. The computer-readable medium of claim 7, further comprising a display routine for displaying a spatial compound image.

9. The computer-readable medium of claim 7, wherein said motion estimation routine selects said previous frame from one of a temporally adjacent frame, a spatially adjacent frame, a last same-angle frame, and a last compounded image.

10. A system for spatial compound ultrasound imaging, said system comprising:
   a frame buffer to store a plurality of frames to form a compound ultrasound image;
   a memory to store data including a motion estimate; and
   a processor configured to estimate motion between a new frame and a previous frame from said frame buffer, wherein said processor is to correct frames in said frame buffer based on updated motion information determined from a previously stored motion information and a motion estimate formed in real time from said new frame and said previous frame, wherein said processor is to apply spatially variant shading to frame data in said frame buffer, wherein said processor is to align frames in said frame buffer to said new frame based on said updated motion information, and wherein said processor is to combine frames in said frame buffer to form a spatial compound image.

11. The system of claim 10, wherein said new frame replaces an oldest frame in said frame buffer.

12. The system of claim 10, wherein said processor sums frames in said frame buffer to form said spatial compound image.

13. The system of claim 10, wherein said processor selects said previous frame from one of a temporally adjacent frame, a spatially adjacent frame, a last same-angle frame, and a last compounded image.

14. The system of claim 10, wherein said processor models said estimated motion as at least one of rigid, affine and elastic.

15. The method of claim 1, wherein said estimated motion represents only a motion estimate between said new image frame and said previous image frame.

16. The method of claim 1, wherein motion from frame j to frame i is represented as $U_{ij}$, motion from frame i to frame j is $U_{ji}=U_{ij}^{-1}$, and alignment is made by $f_j'=U_{ij}f_j$, where $f_j$ is the original frame and $f_j'$ is the frame j aligned to frame i, wherein said new image frame is represented as n+1, said motion estimate is represented as $U_{(n+1)j}$, where j is a chosen previous frame, and said updated motion information is computed by $$U_{(n+1)i} = \begin{cases} U_{(n+1)j}U_{nj}^{-1}U_{ni} & i=n, n-1, \ldots \\ 1 & i=n+1 \end{cases}.$$

17. The method of claim 16, further comprising applying spatially variant shading to said image frames in said frame buffer, and wherein said aligned image frame data and shading are summed and the compound image calculated by normalizing the frame sum using the shading sum:

$$f_c = \frac{\sum_i U_{(n+1)i}(w_i f_i)}{\sum_i U_{(n+1)i} w_i}.$$

18. The system of claim 10, wherein said motion estimate represents only a motion estimate between said new frame and said previous frame.

* * * * *